US010520402B2

(12) United States Patent
Zhang et al.

(10) Patent No.: US 10,520,402 B2
(45) Date of Patent: Dec. 31, 2019

(54) SAMPLE COLLECTING AND INTRODUCING DEVICE AND DETECTION SYSTEM

(71) Applicants: TSINGHUA UNIVERSITY, Beijing (CN); NUCTECH COMPANY LIMITED, Beijing (CN)

(72) Inventors: Qingjun Zhang, Beijing (CN); Yuanjing Li, Beijing (CN); Zhiqiang Chen, Beijing (CN); Ziran Zhao, Beijing (CN); Yinong Liu, Beijing (CN); Yaohong Liu, Beijing (CN); Ge Li, Beijing (CN); Biao Cao, Beijing (CN); Jingli Xie, Beijing (CN); Xiaolin Zhao, Beijing (CN); Qiufeng Ma, Beijing (CN)

( * ) Notice: Subject to any disclaimer, the term of this patent is extended or adjusted under 35 U.S.C. 154(b) by 0 days.

(21) Appl. No.: 16/232,062

(22) Filed: Dec. 26, 2018

(65) Prior Publication Data

US 2019/0195751 A1 Jun. 27, 2019

(30) Foreign Application Priority Data

Dec. 26, 2017 (CN) .......................... 2017 1 1429544

(51) Int. Cl.
*G01N 1/24* (2006.01)
*G01N 1/22* (2006.01)
(Continued)

(52) U.S. Cl.
CPC ............. *G01N 1/24* (2013.01); *G01N 1/2211* (2013.01); *G01N 1/405* (2013.01); *G01N 30/30* (2013.01)

(58) Field of Classification Search
USPC .......................................................... 250/288
See application file for complete search history.

(56) References Cited

U.S. PATENT DOCUMENTS

2004/0089079 A1* 5/2004 Engebretson ........... E21B 49/08 73/863.23
2012/0168617 A1* 7/2012 Chen .................... G01N 27/622 250/282
2017/0016856 A1* 1/2017 Zhang ...................... G01N 1/02

FOREIGN PATENT DOCUMENTS

CN 105277577 A 1/2016
CN 105590827 B 5/2016
CN 106769268 A 5/2017

* cited by examiner

*Primary Examiner* — Kiet T Nguyen
(74) *Attorney, Agent, or Firm* — Kilpatrick Townsend & Stockton, LLP

(57) ABSTRACT

The present disclosure relates to the technical field of safety detection, and in particular to a sample collecting and introducing device and a detection system. The sample collecting and introducing device provided by the present disclosure includes a sampling device for collecting a sample, and a semipermeable membrane device for extracting the sample collected by the sampling device and conveying the extracted sample to detection equipment, wherein the sampling device is provided with an air guide cavity, the air guide cavity is configured to guide airflow carrying the sample to flow to the semipermeable membrane device, the semipermeable membrane device is provided with a semipermeable membrane which is arranged outside the sampling device. In the present disclosure, the size of the semipermeable membrane is no longer limited by the sampling device, and therefore the difficulty of increasing the area of the semipermeable membrane is reduced.

15 Claims, 3 Drawing Sheets

(51) Int. Cl.
*G01N 1/40* (2006.01)
*G01N 30/30* (2006.01)

SAMPLE COLLECTING AND INTRODUCING DEVICE AND DETECTION SYSTEM

CROSS-REFERENCES TO RELATED APPLICATIONS

The present application claims the priority of Chinese Application No. 201711429544.X, filed in the Chinese Patent Office on Dec. 26, 2017, whose entire contents are herein incorporated by reference.

FIELD

The present disclosure relates to the technical field of safety detection, and in particular to a sample collecting and introducing device and a detection system.

BACKGROUND

In order to improve the safety, detection equipment is applied to detect trace substances attached to a detected object, and in order to cooperate with the detection, a sample collecting and introducing device is applied to collect and extract samples attached to the detected object.

At present, there are a variety of sample collecting and introducing devices. As one of them, the sample collecting and introducing device comprises a sampling device and a semipermeable membrane device, wherein the sampling device sweeps the detected object via airflow to collect samples and conveys the collected samples to the semipermeable membrane device through an air guide cavity, and the semipermeable membrane device extracts the samples via a semipermeable membrane and conveys the extracted samples to the detection equipment for detection. As the samples are extracted by the semipermeable membrane, not only the instrument contamination can be prevented, but also an enrichment function can be played on the samples to improve the sampling efficiency. The larger the area of the semipermeable membrane is, the more favorable to improve the sampling efficiency it is.

However, in the prior art, the semipermeable membrane is usually arranged inside the sampling device. In this case, to increase the area of the semipermeable membrane, the size of a structural component of the sampling device outside of the semipermeable membrane has to be increased accordingly, which is difficult, and increases the weight and the volume of the entire sample collecting and introducing device, thus making the sample collecting and introducing device inconvenient to use.

SUMMARY

One technical problem to be solved by the present disclosure is to reduce the difficulty of increasing the area of a semipermeable membrane of a sample collecting and introducing device.

In order to solve the above technical problem, on one side the present disclosure provides a sample collecting and introducing device, comprising:

a sampling device, for collecting a sample; and a semipermeable membrane device, for extracting the sample collected by the sampling device and introducing the extracted sample to detection equipment;

wherein the sampling device is provided with an air guide cavity which is configured to guide airflow carrying the sample to flow to the semipermeable membrane device, the semipermeable membrane device is provided with a semipermeable membrane, and the semipermeable membrane is arranged at the outside of the sampling device.

According to some embodiments of the disclosure, the semipermeable membrane device further comprises a holding member for holding the semipermeable membrane, and a first space located at one side of the semipermeable membrane and a second space located at the other side of the semipermeable membrane exist between the holding member and the semipermeable membrane, wherein the air guide cavity guides the airflow carrying the sample to flow into the first space, the sample carried by the airflow flowing into the first space enters the second space after being desorbed by the semipermeable membrane, and the second space is in fluid communication with the detection equipment.

According to some embodiments of the disclosure, at least one of a concave part and a convex part is provided on a side surface of the holding member adjacent to the semipermeable membrane.

According to some embodiments of the disclosure, the semipermeable membrane device further comprises an air pump, the air pump is in fluid communication with the first space to discharge the airflow that does not penetrates through the semipermeable membrane to the outside of the first space.

According to some embodiments of the disclosure, the semipermeable membrane device further comprises a gas supply device, the gas supply device is in fluid communication with the second space to inject a carrier gas into the second space, and the carrier gas flows to the detection equipment after being mixed with the sample that is desorbed by the semipermeable membrane and enters the second space.

According to some embodiments of the disclosure, the semipermeable membrane device further comprises a filtering device, the filtering device is arranged on a communication passage between the gas supply device and the second space to filter the carrier gas flowing from the gas supply device to the second space.

According to some embodiments of the disclosure, the semipermeable membrane device further comprises a temperature control device, the temperature control device is configured to heat and cool the semipermeable membrane, so that the semipermeable membrane device enriches the sample at a relatively low temperature and desorbs the sample at a relatively high temperature.

According to some embodiments of the disclosure, the semipermeable membrane device enriches (or extracts) the sample at a relatively low temperature and desorbs the sample at a relatively high temperature.

According to some embodiments of the disclosure, the sample collecting and introducing device further comprises a sample introducing tube, and the sample introducing tube is connected between the air guide cavity and the semipermeable membrane device.

According to some embodiments of the disclosure, the semipermeable membrane device is arranged at the outside of the sampling device.

According to some embodiments of the disclosure, the sampling device comprises an ejection part, the ejection part is configured to sweep the sample attached to the detected object through the airflow, and the swept sample flows to the air guide cavity under the drive of the airflow.

According to some embodiments of the disclosure, the ejection part comprises an air pump, an air ejection cavity and an ejection hole, which are in fluid communication with each other successively, and the air pumped by the air pump is ejected toward the detected object through the air ejection cavity and the ejection hole.

According to some embodiments of the disclosure, the sampling device further comprises a cyclone generation part, and the cyclone generation part is configured to generate cyclone and drive the sample swept by the ejection part to flow to the air guide cavity via the generated cyclone.

According to some embodiments of the disclosure, the cyclone generation part comprises an air supplementing pump, an air supplementing cavity and a swirling hole, which are in fluid communication with each other successively, the air supplementing pump pumps airflow into the air supplementing cavity, and the swirling hole rotationally ejects the airflow entering the air supplementing cavity to form the cyclone.

According to some embodiments of the disclosure, the swirling hole extends from the air supplementing cavity to the outer surface of the sampling device.

Another aspect of the present disclosure further provides a detection system, including detection equipment and the sample collecting and introducing device of the present disclosure, and the semipermeable membrane device of the sample collecting and introducing device is in fluid communication with the detection equipment.

According to the sample collecting and introducing device provided by the disclosure, the semipermeable membrane is arranged at the outside of the sampling device, so that the size of the semipermeable membrane is no longer limited by the sampling device, and therefore, it becomes less difficult to increase the area of the semipermeable membrane.

Other embodiments of the present disclosure and the advantages thereof will become apparent from the following detailed description of the exemplary embodiments of the present disclosure with reference to the drawings.

BRIEF DESCRIPTION OF THE DRAWINGS

To illustrate technical solutions in the embodiments of the present disclosure or in the prior art more clearly, a brief introduction on the drawings which are needed in the description of the embodiments or the prior art is given below. Apparently, the drawings in the description below are merely some of the embodiments of the present disclosure, based on which other drawings can be obtained by those of ordinary skill in the art without any creative effort.

DETAILED DESCRIPTION OF THE INVENTION

Figure 1:
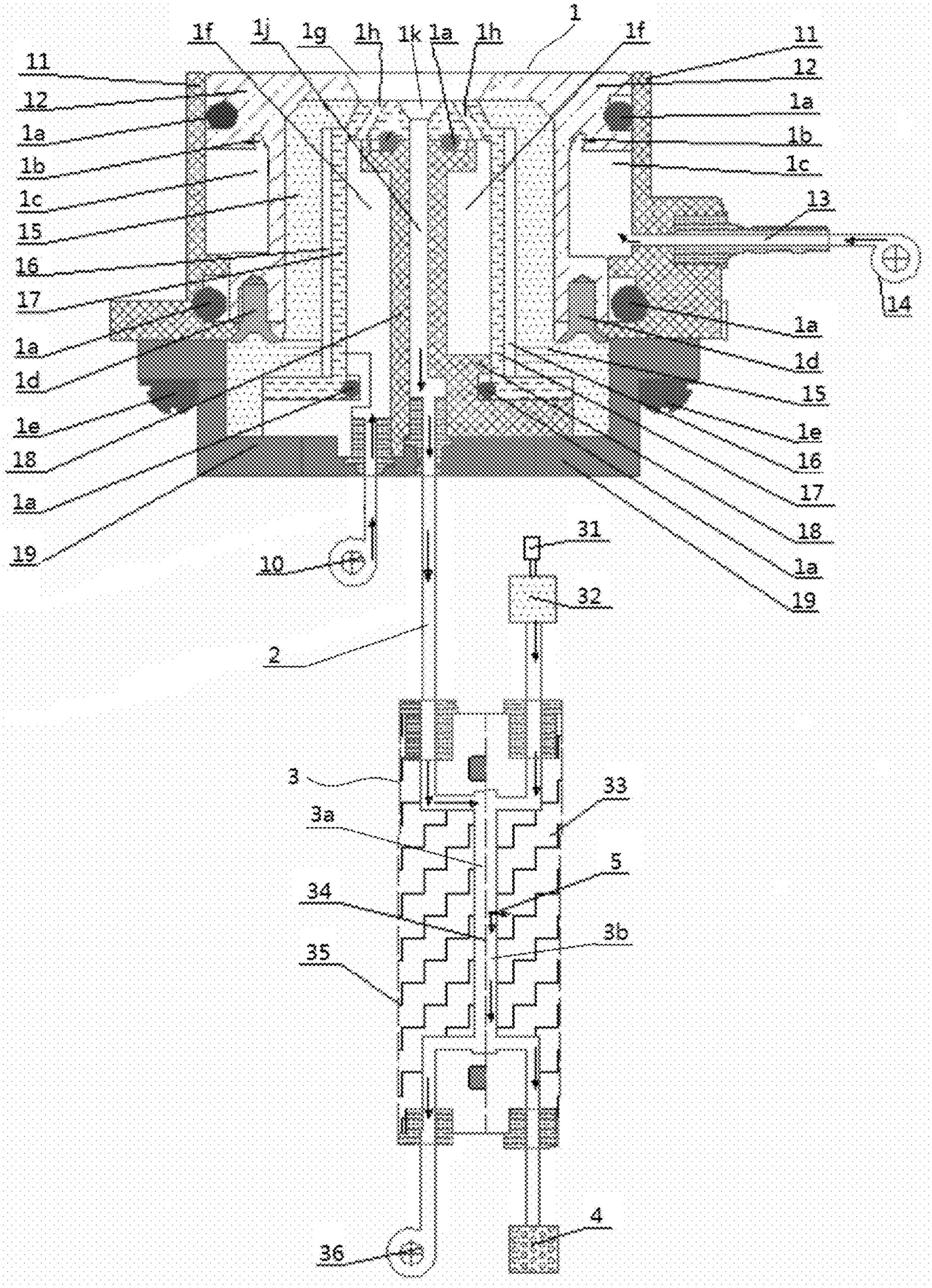
FIG. 1 shows a longitudinal section schematic diagram of a sample collecting and introducing device in an embodiment of the present disclosure.

A clear and complete description of technical solutions in the embodiments of the present disclosure will be given below, in combination with the drawings in the embodiments of the present disclosure. Apparently, the embodiments described below are merely a part, but not all, of the embodiments of the present disclosure. The following description of at least one exemplary embodiment is merely illustrative, and is in no way to serve as any limitation to the present disclosure or the application or use thereof. All of other embodiments, obtained by those of ordinary skill in the art based on the embodiments of the present disclosure without any creative effort, fall into the protection scope of the present disclosure.

Techniques, methods and equipment known to those of ordinary skill in the relevant art may not be discussed in detail, but where appropriate, the techniques, methods and equipment should be considered as a part of the specification as granted.

In the description of the present disclosure, it should be understood that orientations or positional relationships indicated by orientation words such as “front, back, upper, lower, left, right”, “lateral, vertical, perpendicular, horizontal” and “top, bottom” and the like are generally based on the orientations or positional relationships shown in the drawings, and are merely for the convenience describing the present disclosure and simplifying the description, the above orientation words are not intended to indicate or imply that the devices or elements referred to must have particular orientations or be constructed and operated in particular orientations, if not otherwise stated, and thus cannot be construed as limitations to the protection scope of the present disclosure; and the orientation words “inside and outside” refer to the inside and the outside of the contours of the components themselves.

In the description of the present disclosure, it should be understood that parts and components are defined by such words as “first”, “second” and the like merely for the purpose of facilitating the distinction of the corresponding parts and components, and if not otherwise stated, the above words have no particular meaning, and thus cannot be construed as limitations to the protection scope of the present disclosure.

FIGS. 1 to 4 illustrate an embodiment of the sample collecting and introducing device of the present disclosure. With reference to FIG. 1 to FIG. 4, the sample collecting and introducing device provided by the present disclosure comprises a sampling device 1 for collecting a sample, and a semipermeable membrane device 3 for extracting the sample collected by the sampling device 1 and introducing the extracted sample to detection equipment 4, wherein the sampling device 1 is provided with an air guide cavity **1*j*, which is configured to guide airflow carrying the sample to flow to the semipermeable membrane device 3, the semipermeable membrane device 3 is provided with a semipermeable membrane 34, and the semipermeable membrane 34 is arranged at the outside of the sampling device 1**.

In the present disclosure, the semipermeable membrane 34 of the sample collecting and introducing device is arranged at the outside of the sampling device 1, so that the size of the semipermeable membrane 34 is no longer limited by the sampling device 1, and thus the difficulty of increasing the area of the semipermeable membrane 34 can be reduced, which is favorable to improve the sampling efficiency and the user experience.

The present disclosure is further described below with reference to the embodiment as shown in FIGS. 1 to 4.

As shown in FIGS. 1 to 4, in the embodiment, the sample collecting and introducing device comprises a sampling device 1, a sample introducing tube 2 and a semipermeable membrane device 3. The sampling device 1 is configured to collect the sample attached to a detected object 6 by sweeping the detected object 6 with airflow and convey the collected sample to the semipermeable membrane device 3;

the semipermeable membrane device 3 is configured to extract the sample collected by the sampling device 1 and convey the sample to the detection equipment 4 for detection. In the embodiment, the semipermeable membrane device 3 is arranged at the outside of the sampling device 1 and is connected with the sampling device 1 through the sample introducing tube 2. The sample attached to the detected object 6 may be a volatile substance, a semi-volatile substance and a surface contaminant in the detected object 6 and may be a trace substance in various forms such as granule or powder.

As shown in FIG. 1, the sampling device 1 of the embodiment comprises an ejection part and a flow guide part, the ejection part is configured to sweep off the sample attached to the detected object 6 through the airflow; and the flow guide part communicates with the semipermeable membrane device 3 to introduce the sample swept by the ejection part to flow to the semipermeable membrane device 3.

Figure 2:
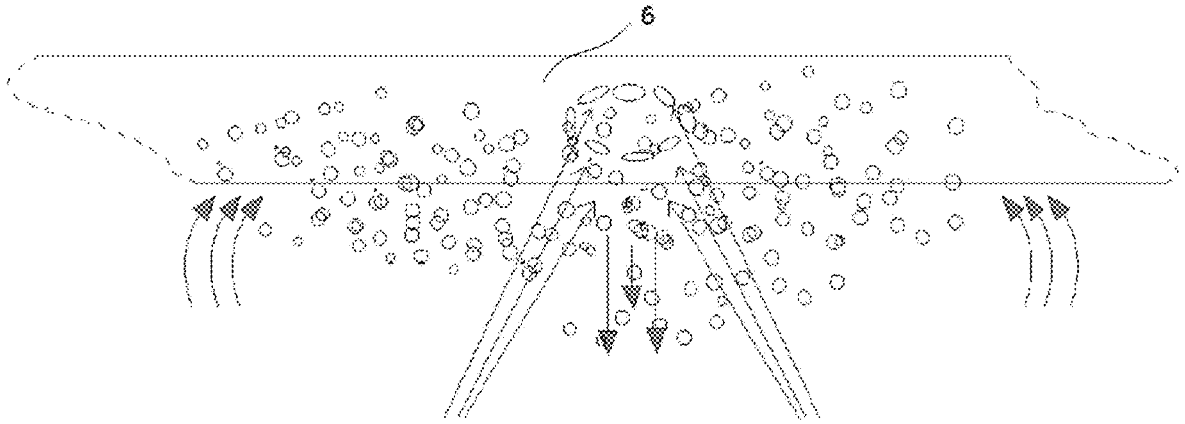
FIG. 2 shows a schematic diagram of a state in which the sample collecting and introducing device as shown in FIG. 1 collects a sample from a detected object.

It can be seen in combination with FIG. 1 and FIG. 2, in the embodiment, the ejection part comprises an air pump 10, an air ejection cavity 1*f* and an ejection hole 1*h*, which are in fluid communication with each other successively, wherein the air pump 10 pumps the air to ejected toward the detected object 6 through the air ejection cavity 1*f* and the ejection hole 1*h*. The flow guide part comprises an air guide cavity 1*j*, and the air guide cavity 1*j* is in fluid communication with the ejection part and the semipermeable membrane device 3. Based on this, the ejection hole 1*h* injects the airflow onto the detected object 6, the airflow can impact and sweep the samples attached to the detected object 6, so that the samples are swept off from the detected object 6 and are carried by the airflow to flow to the semipermeable membrane device 3 through the air guide cavity 1*j*, thereby realizing the collection of the samples. Realizing sample collection by means of air sweeping is clean, pollution-free, and conducive to shortening the sample diffusion time and improving the collection efficiency.

Furthermore, in order to improve the collection efficiency of samples with a high boiling point, as shown in FIG. 1, in the embodiment, the ejection part further comprises a heating device 16 and a heat preservation device 15. The heating device 16 is configured to heat the air in the air ejection cavity 1*f*, so that the ejection part can sweep the samples on the detected object 6 via hot airflow, which can make samples with high boiling point be more conveniently driven to deviate from the detected object 6, thus the collection of the samples with high boiling point is realized, the risk of leak collection and leak detection of the samples with high boiling point is reduced, the sample collection range is widened, and the collection efficiency is improved. Moreover, as the hot airflow can promote samples in granular and cluster form to disperse into single molecules, therefor sweeping the samples with the hot airflow can make the samples enter the semipermeable membrane device 3 more fully in the form of the single molecules, which not only can reduce the detection limit of the samples with high boiling point, but also can improve the enrichment and desorption efficiency of the semipermeable membrane device 3 and the detection sensitivity of the detection encampment 4. The heating device 16 may be implemented in various structural forms such as a heating sheet, a heating wire or a heating belt. The heat preservation device 15 is configured to perform heat preservation on the air in the air ejection cavity 1*f*, in this case, the ejection part can be conveniently kept at a desired temperature, so that the ejection part can continuously eject the airflow with a preset temperature to the detected object 6, which further improves the working reliability of the ejection part.

Further, in order to further improve the collection efficiency, the sampling device 1 of the embodiment further comprises a cyclone generation part, and the cyclone generation part is configured to generate cyclone and drive the sample swept by the ejection part to flow to the air guide cavity 1*j* via the generated cyclone. As shown in FIG. 1, the cyclone generation part of the embodiment comprises an air supplementing pump 14, an air supplementing cavity 1*c* and a swirling hole 1*b*, which are in fluid communication with each other successively, wherein the air supplementing pump 14 pumps airflow into the air supplementing cavity 1*c*, and the swirling hole 1*b* rotationally ejects the airflow entering the air supplementing cavity 1*c* to form the cyclone. The cyclone generated by the cyclone generation part is similar to a tornado, which can generate a negative pressure center with a large negative pressure above the air guide cavity 1*j*, and the negative pressure center can suck the sample swept by the ejection part, so that the sample swept by the ejection part can flow to the semipermeable membrane device 3 via the flow guide cavity 1*j* more efficiently and more smoothly, thereby improving the sample collection efficiency.

Figure 3:
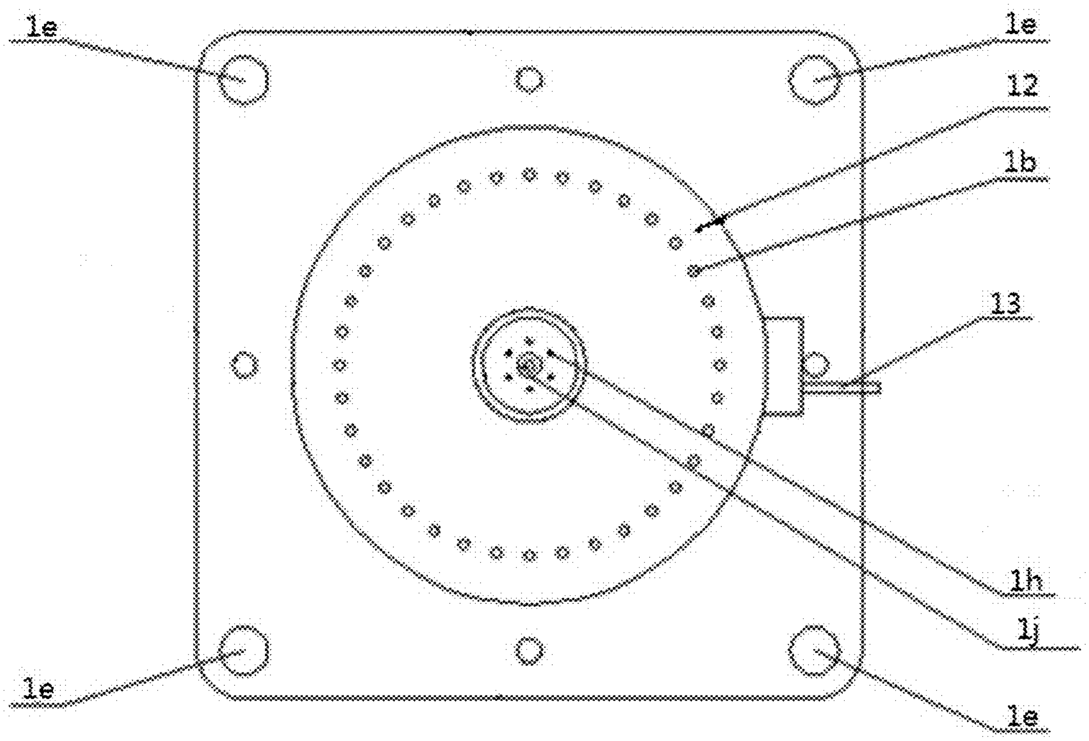
FIG. 3 shows a top view of the sample collecting and introducing device as shown in FIG. 1.

Specifically, as shown in FIG. 1 and FIG. 3, the sampling device 1 of the embodiment comprises a shell, and the shell comprises an outer cavity body 11, an upper cover 12 and a bottom cover 19. The outer cavity body 11 is hollow and opens at both upper end and lower end. The upper cover 12 covers the upper opening of the outer cavity body 11. The bottom cover 19 covers the lower opening of the outer cavity body 11. The bottom cover 19 is connected with the outer cavity body 11 by a second screw 1*e*. The shell provides a mounting base for other structural components of the sampling device 1 and provides a certain supporting and protecting function for the other structural components of the sampling device 1 located in the shell. The air ejection cavity 1*f*, the ejection hole 1*h*, the air guide cavity 1*j*, the heating device 16, the heat preservation device 15, the air supplementing cavity 1*c* and the swirling hole 1*b* are all disposed inside the shell.

It can be seen from FIG. 1 that the sampling device 1 of the embodiment further comprises an air ejection cavity body 17 and an air guide cavity body 18 disposed in the shell, the air ejection cavity 1*f* locates between the air ejection cavity body 17 and the shell, and the air guide cavity 1*i* locates between the air guide cavity body 18 and the shell. More specifically, as shown in FIG. 1, the air ejection cavity body 17 and the air guide cavity body 18 are arranged inside the upper cover 12; the air ejection cavity body 17 and the air guide cavity body 18 are both provided with hollow cavities therein and both open at a lower end; the air guide cavity body 18 is located in the air ejection cavity body 17; the bottom cover 19 that covers the lower opening of the outer cavity body 11 also covers the lower opening of the air ejection cavity body 17 and the air guide cavity body 18; the heating device 16 is arranged on the outer surface of the air ejection cavity body 17; and the heat preservation device 15 is arranged at the outside of the heating device 16 and is located between the heating device 16 and the inner wall of the upper cover 12. The heat preservation device 15 is connected with the upper cover 12 via a first screw 1*d*. In this case, the air guide cavity body 18 and the bottom cover 19 enclose the air guide cavity 1*j*; the heat preservation device 15, the air ejection cavity body 17, the air guide cavity body 18 and the bottom cover 19 enclose the air ejection cavity 1*f*; and the air guide cavity 1*j* is located in the air ejection cavity 1*f*, in other words, the air guide cavity 1*j* is located at the middle of the sampling device 1. Since the sample swept by the ejection part converges toward the middle of the air ejection cavity 1*f* under the action of the airflow, the air guide cavity 1*j* located at the middle of the sampling device 1 can more conveniently and efficiently guide the airflow carrying the sample to flow to the semi-permeable membrane device 3. Of course, the air ejection cavity 1*f* may not be enclosed by the heat preservation device 15, the air ejection cavity body 17, the air guide cavity body 18 and the bottom cover 19, for example, the air ejection cavity 1*f* may be directly enclosed by the air ejection cavity body 17, the air guide cavity body 18 and the bottom cover 19.

In addition, as can be seen from FIG. 1, the bottom cover 19 is provided with an opening at a position corresponding to the air guide cavity 1*j*, so as to facilitate fluid communication between the air guide cavity 1*j* and the semipermeable membrane device 3. Further, the bottom cover 19 is also provided with an opening at a position corresponding to the air ejection cavity 1*f*, so as to facilitate fluid communication between the air ejection cavity 1*f* and the air pump 10. In the embodiment, the air pump 10 and the sample introducing tube 2 are both arranged outside the shell and below the bottom cover 19. The air pump 10 is in fluid communication with the air ejection cavity 1*f* via an air tube. The sample introducing tube 2 extend downward from the air ejection cavity 1*f* to communicate with the semipermeable membrane device 3, thereby realizing fluid communication between the air guide cavity 1*j* and the semipermeable membrane device 3. Connecting the sampling device 1 and the semipermeable membrane device 3 with the sample introducing tube 2 can facilitate the disassembly and assembly of the sampling device 1 and the semipermeable membrane device 3, and particularly can make the maintenance and replacement of the semipermeable membrane device 3 more convenient and quicker.

The ejection hole 1*h* is located on the air ejection cavity body 17. As shown in FIG. 1 and FIG. 3, in the embodiment, a plurality of ejection holes 1*h* are disposed on the top of the air ejection cavity body 17 at intervals along the circumferential direction of the air ejection cavity body 17. The ejection hole 1*h* is in fluid communication with the air ejection cavity 1*f* and in fluid communication with the external environment above the air guide cavity 1*j*, so as to eject the air in the air ejection cavity 1*f* to the detected object 6 above the air guide cavity 1*j* to impact the sample attached to the detected object 6. As can be seen from FIG. 1, in the embodiment, the ejection hole 1*h* is located at the outer side of the air guide cavity 1*j*, and is inclined toward the middle of the air ejection cavity 1*f* (namely inclined toward the central axis of the air guide cavity 1*j*) along the direction in which the airflow flows from the air ejection cavity 1*f* to the detected object 6 (namely the direction from bottom to top in FIG. 1), in this way, the swept sample can be driven to converge toward the middle of the air ejection cavity 1*f*, which is on one hand convenient for the sample to flow into the air guide cavity 1*j* located at the middle of the air ejection cavity 1*f*, and on the other hand convenient for the ejection part to better cooperate with the cyclone generation part, enabling the sample to be more fully sucked by the cyclone generated by the cyclone generation part.

The air supplementing cavity 1*c* is formed between the outer cavity body 11 and the upper cover 12. As can be seen from FIG. 1, in the embodiment, the lower end of the upper cover 12 extends into the outer cavity body 11 and is enclosed with the outer cavity body 11 to form the air supplementing cavity 1*c*. An air supplementing tube 13 is arranged on the outer cavity body 11, one end of the air supplementing tube 13 is in fluid communication with the air supplementing cavity 1*c*, and the other end of the air supplementing tube 13 is in communication with the air supplementing pump 14, so that the air supplementing pump 14 is in fluid communication with the air supplementing cavity 1*c* through the air supplementing tube 13, and the air supplementing pump 14 can pump the air into the air supplementing cavity 1*c* through the air supplementing tube 13. Of course, the air supplementing tube 13 can be omitted, and the air supplementing cavity 1*c* may be in direct fluid communication with the air supplementing pump 14 or may communicate with the air supplementing pump 14 through other communication members.

The swirling hole 1*b* is located on the upper cover 12 and outside the ejection hole 1*h* and the air guide cavity 1*j*. So far, as shown in FIG. 1, along the direction that from the central axis of the air guide cavity 1*j* to the outer side of the air guide cavity 1*j*, the air guide cavity 1, the ejection hole 1*h* and the swirling hole 1*b* are successively arranged. Moreover, as shown in FIG. 1, in the embodiment, a plurality of swirling holes 1*b* are arranged on the upper cover 12 at intervals along the circumferential direction of the upper cover 12*b*. Each swirling hole 1*b* is arranged obliquely, the central axis of the swirling hole 1*b* and the central axis of the air supplementing cavity 1*c* are non-coplanar, and the inclination angles of the respective swirling holes 1*b* are approximately the same. Based on this, the airflow ejected from the swirling hole 1*b* rotates at a certain angle with x direction, y direction and z direction, thus generating a cyclone which further drives the flow of the external airflow to amplify the airflow to form a cyclone similar to a tornado, thereby forming a negative pressure center above the air guide cavity 1*j*. In the embodiment, the swirling hole 1*b* extends from the air supplementing cavity 1*c* to the outer surface of the sampling device 1, in this case, the swirling hole 1*b* is in direct fluid communication with the external environment of the sampling device 1, so that the swirling hole 1*b* can directly and rotationally eject the airflow into the external environment of the sampling device 1. Specifically, the swirling hole 1*b* extends from the air supplementing cavity 1*c* to the upper surface of the upper cover 12 and is in fluid communication with the external environment above the air guide cavity 1*j*, so that the negative pressure center of the cyclone is formed above the air guide cavity 1*j*, which enables the sample swept by the ejection part 1*b* to be better sucked into the air guide cavity 1*j* by the cyclone.

Moreover, as shown in FIG. 1, in the embodiment, the sampling device 1 further comprises a sample suction port, and the sample suction port communicates the air guide cavity 1*j* with the external environment to guide the airflow carrying the sample flow to the air guide cavity 1*j*. It can be seen from FIG. 1 that the sample suction port of the embodiment comprises a first sample suction port 1*g* and a second sample suction port 1*k*, wherein, the first sample suction port 1*g* is arranged on the top of the upper cover 12 and communicates the external environment with the second sample suction port 1*k* and the ejection hole 1*h*, besides, the first sample suction port 1*g* is of a tapered horn shape from top to bottom; while the second sample suction port 1*k* is arranged on the top of the air ejection cavity body 17 and communicates the first sample suction port 1*g* with the air guide cavity 1*j*, besides, the second sample suction port 1*k* is of a tapered horn shape from top to bottom. The edge of a bottom surface (the surface with the minimum cross sectional area) of the first sample suction port 1*g* is located on the outer side of the ejection hole 1*h*; and the edge of a top face (the surface with the maximum cross sectional area) of the second sample suction port 1*k* is located on the inner side of the ejection hole 1*h*. Based on the setting, the first sample suction port 1*g* and the second sample suction port 1*k* are successively arranged along the direction in which the airflow flows from the detected object 6 to the air guide cavity 1*j* (namely the direction from top to bottom in FIG. 1); furthermore, along the direction in which the airflow flows from the detected object 6 to the air guide cavity 1*j*, the cross sectional area of the first sample suction port 1*g* and that of the second sample suction port 1*k* both decrease; and meanwhile, the minimum cross sectional area of the first sample suction port 1*g* is greater than the maximum cross sectional area of the second sample suction port 1*k*. In this way, along the direction in which the airflow flows from the detected object 6 to the air guide cavity 1*j*, the cross sectional area of the sample suction port decreases, specifically is in the shape of a tapered horn. As the radius of the cyclone generated by the cyclone generation part of the sampling device 1 in the embodiment decreases from top to bottom, therefore, the sample suction port with reduced cross sectional area from top to bottom is more adapted to the characteristics of the cyclone airflow, so as to better guide the sample to flow to the air guide cavity 1*j* under the suction of the cyclone airflow.

In order to improve the airtightness of the sampling device 1, as shown in FIG. 1, the sampling device 1 of the embodiment further comprises a plurality of sealing rings 1*a*. Specifically, as can be seen from FIG. 1, the sealing rings 1*a* are arranged between the outer wall of the upper cover 12 and the inner wall of the outer cavity body 11 to improve the airtightness of the air supplementing cavity 1*c*; and the sealing rings 1*a* are arranged between the air ejection cavity body 17 and the air guide cavity body 18 to improve the airtightness of the air ejection cavity 1*f*.

As can be seen from the above description of the sampling device 1, the sampling device 1 of the embodiment sweeps the sample from the detected object 6 via the airflow ejected by the ejection part, promotes the swept sample to flow into the air guide cavity 1*j* through the sample suction port via the cyclone generated by the cyclone generation part, and then guides the airflow carrying the sample to enter the semipermeable membrane device 3 for extraction by means of the air guide cavity 1*j*.

The semipermeable membrane device 3 enriches and desorbs the sample collected by the sampling device 1 via the semipermeable membrane 34, and then conveys the sample to the detection equipment 4. As shown in FIG. 1, in the embodiment, the semipermeable membrane device 3 comprises the semipermeable membrane 34, a holding member 33, a temperature control device 35, an air pump 36, a gas supply device 31 and a filtering device 32.

The semipermeable membrane 34, which is selective for the permeation of different particles, allows only the desired particles to permeate. In the embodiment, the semipermeable membrane 34 is capable of preventing the permeation of impurities such as water molecules and ammonia molecules, and restricting the formation of cluster molecules, thereby being conducive to improving the detection sensitivity of the detection equipment 4.

The holding member 33 is configured to hold the semipermeable membrane 34. As shown in FIG. 1, in the embodiment, the first space 3*a* located at one side of the semipermeable membrane 34 and the second space 3*b* located at the other side of the semipermeable membrane 34 are formed between the holding member 33 and the semipermeable membrane 34. The air guide cavity 1*j* guides the airflow carrying the sample to flow into the first space 3*a*, and after being extracted by the semipermeable membrane 34, the sample carried by the airflow flowing into the first space 3*a* enters the second space 3*b* which is in fluid communication with the detection equipment 4. Specifically, the air guide cavity 1*j* communicates with the first space 3*a* through the sample introducing tube 2. Thus, the sample collected by the sampling device 1 can enter the first space 3*a* via the sample introducing tube 2, permeate through the second space 3*b* after being enriched and desorbed by the semipermeable membrane 34, and finally flow into the detection equipment 4 to complete the detection.

The temperature control device 35 is configured to heat and cool the semipermeable membrane 34. The semipermeable membrane 34 enriches the samples at a lower temperature and desorbs the samples at a higher temperature. By setting the temperature control device 35, the semipermeable membrane 34 can be controlled to cooperate with the sampling device 1 to realize a sample enrichment and desorption process. Before the sampling device 1 finish collecting samples, the semipermeable membrane 34 can be cooled by the temperature control device 35, so that sample molecules 5 capable of penetrating through the semipermeable membrane 34 are adsorbed on the semipermeable membrane 34 to achieve sample enrichment; and after the sampling device 1 completes the sampling, the semipermeable membrane 34 can be heated by the temperature control device 35 to release the sample molecules 5 adsorbed on the semipermeable membrane 34, and then the sample molecules flow to the detection equipment 4 through the second space 3*b*. As shown in FIG. 1, in order to facilitate the arrangement of the temperature control device 35, the temperature control device 35 of the embodiment is arranged on the outer surface of the holding member 33, and indirectly heats and cools the semipermeable membrane 34 by heating and cooling the holding member 33. Based on this, the holding member 33 can be made of an inert metal material with good thermal conductivity to facilitate the heat transfer. The temperature control device 35 may comprise a heating device and a cooling device. The heating device may comprise a heating wire, a heating belt, a heating sheet or the like. The cooling device may comprise a semiconductor refrigeration device or the like.

The air pump 36 is in fluid communication with the first space 3*a* for discharging the airflow that does not penetrates through the semipermeable membrane 34 to the outside of the first space 3*a*, so as to achieve the cleaning purpose. By setting the air pump 36, the discharge speed of the substance that does not penetrates through the semipermeable membrane 34 can be accelerated, and the cleaning efficiency is improved. Specifically, as can be seen from FIG. 1, the air pump 36 and the detection equipment 4 are respectively connected to the lower portions of the first space 3*a* and the second space 3*b*. During operation, the detection equipment 4 is in a negative pressure state and has a certain suction force which is set to be greater than that of the air pump 36.

The air supply device 31 is in fluid communication with the second space 3*b* to inject the carrier gas into the second space 3*b*, and the carrier gas is mixed with the sample entering into the second space 3*b* after being desorbed by the semipermeable membrane 34 and then flows to the detection equipment 4. By setting the gas supply device 31, the sample molecules 5 penetrating through the semipermeable membrane 34 can be further driven to flow to the detection equipment 4 by the carrier gas, so that the speed of the desorbed sample molecules 5 to flow to the detection equipment 4 is accelerated, and then the detection efficiency is improved.

The filtering device 32 is arranged on a communication path between the gas supply device 31 and the second space 3*b* to filter the carrier gas flowing from the gas supply device 31 to the second space 3*b*. The filtering device 32 is configured to filter the carrier gas provided by the gas supply device 31 to remove impurities such as moisture in the carrier gas, thereby the purity of the sample sent to the detection equipment 4 being further improved, which is conducive to improving the detection accuracy and the detection sensitivity.

The working process of the sample collecting and introducing device in the embodiment may be carried out as follows:

When sampling, the air pump 10 below the air ejection cavity 1*f* work in a pulse manner, so that the airflow ejected from the ejection hole 1*h* impacts the detected object 6 in the pulse manner to sweep the sample down. In the process, the air supplementing pump 14 communicating with the air supplementing cavity 1*c* through the air supplementing tube 13 keeps on, the swirling hole 1*b* keeps blowing air, so that under the suction of the negative pressure center of the cyclone generated by the cyclone generation part and the air pump 36 located at the bottom of the first space 3*a*, the swept sample molecules enter the first space 3*a* of the semipermeable membrane device 3 through the air guide cavity 1*j*, at this time, the semipermeable membrane 34 is in a low temperature state under the refrigeration of the temperature control device 35, the majority of the sample molecules are adsorbed on the semipermeable membrane 34 after entering the first space 3*a* to realize sample enrichment, and water molecules and the like which cannot be adsorbed by the semipermeable membrane 34 are discharged to the outside of the first space 3*a* by the air pump 36 at the lower end of the semipermeable membrane device 3 to achieve the purpose of preliminary cleaning; after the collection is performed for a certain period of time, the semipermeable membrane 34 is rapidly heated by the temperature control device 35, so that the sample adsorbed on the semipermeable membrane 34 is desorbed from the semipermeable membrane 34, the desorbed sample molecules 5 enter the detection equipment 4 for detection under the action of the negative pressure of the detection equipment 4 and the driving of the carrier gas provided by the gas supply device 31, meanwhile the temperature control device 35 rapidly cools the holding member 33 to perform a next sampling process.

In addition, as can be seen from FIG. 1, the semipermeable membrane device 3 of the embodiment is integrally arranged outside the shell of the sampling device 1, that is, not only the semipermeable membrane 34 is located outside the shell of the sampling device 1, but also other parts of the semipermeable membrane device 3, such as the holding member 33, the air pump 36, the heat preservation device 35, the gas supply device 31 and the filtering device 32, are located outside the shell of the sampling device 1.

In the embodiment, the advantages of the semipermeable membrane device 3 being integrally arranged outside the sampling device 1 lie that, on one hand, the semipermeable membrane device 3 and the sampling device 1 are relatively independent with each other, so that it's easier to separately disassemble, maintain and improve the semipermeable membrane device 3 and the sampling device 1, and particularly, it is convenient to replace the semipermeable membrane 34 that needs to be replaced frequently; on the other hand, the semipermeable membrane 34 is located at the outside of the sampling device 1, the size of the semipermeable membrane 34 is no longer limited by the sampling device 1, and when the area of the semipermeable membrane 34 is increased, the sizes of the air guide cavity body 18, the air ejection cavity body 17, the heating device 16, the heat preservation device 15, and the shell do not need to be increased accordingly, therefore the area of the semipermeable membrane 34 can be conveniently increased on the premise of not excessively increasing the volume and the weight of the sample collecting and introducing device, and as the contact area between the sample and the semipermeable membrane 34 can be increased by increasing the area of the semipermeable membrane 34, the sample collection efficiency can be more conveniently improved.

Figure 4:
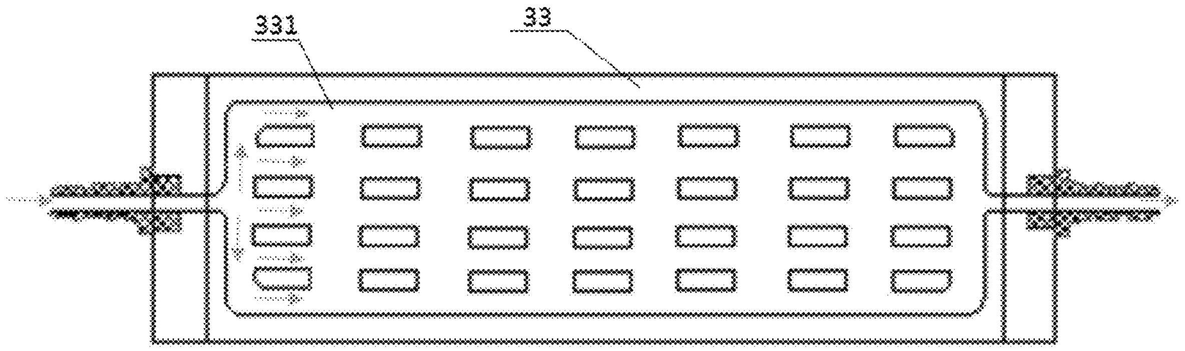
FIG. 4 shows a structural schematic diagram of a holding member.

Moreover, in order to further improve the sample extraction rate of the semipermeable membrane device 3, as shown in FIG. 1 and FIG. 4, in the embodiment, a concave part 331 is further arranged on one side surface of the holding member 33 adjacent to the semipermeable membrane 34. As the concave part 331 is arranged on the inner surface of the holding member 33, the area of the inner surface of the holding member 33 is increased, thereby the time of the sample penetrating from one side of the semipermeable membrane 34 (the first space 3*a*) to the other side of the semipermeable membrane 34 (the second space 3*b*) being prolonged, the sample enrichment factor being increased, and the sample enrichment rate being improved. Except for the concave part 331, a convex part may be arranged on the side surface of the holding member 33 close to the semipermeable membrane 34 instead, or the concave part 331 and the convex part may both be arranged on the side surface of the holding member 33 close to the semipermeable membrane 34 at the same time. Actually, as long as the contact area of the airflow and the semipermeable membrane can be increased and the semipermeable membrane 34 can be supported with sufficient strength at the same time, the variations all fall within the protection scope of the present disclosure.

In summary, as described above, based on the sample collecting and introducing device of the present disclosure, the area of the semipermeable membrane 34 can be easily increased, and a sampling and concentration process with a wider boiling point range and higher efficiency can be realized. The sample collecting and introducing device of the present disclosure may be cooperatively used with an ion mobility spectrometer (IMS), a gas chromatograph (GC), a mass spectrometer (MS), a gas chromatograph and ion mobility spectrometer (GC-IMS), a gas chromatograph and mass spectrometer (GC-MS) and other detection equipment 4 to realize onsite real-time detection and analysis of volatile, semi-volatile, surface contaminants and the like, which is of high detection speed detection accuracy. Accordingly, the present disclosure further provides a detection system, including detection equipment 4 and the sample collecting and introducing device of the present disclosure.

The above descriptions are only exemplary embodiments of the present disclosure, and are not intended to limit the present disclosure. Any modifications, equivalent replacements, improvements and the like made within the spirit and principle of the present disclosure should be encompassed within the protection scope of the present disclosure.

What is claimed is:

1. A sample collecting and introducing device, comprising:

a sampling device, for collecting a sample; and a semipermeable membrane device, for extracting the sample collected by the sampling device and introducing the extracted sample to detection equipment;

wherein the sampling device is provided with an air guide cavity which is configured to guide airflow carrying the sample to flow to the semipermeable membrane device, the semipermeable membrane device is provided with a semipermeable membrane, and the semipermeable membrane is arranged at the outside of the sampling device.

2. The sample collecting and introducing device according to claim 1, wherein the semipermeable membrane device further comprises a holding member for holding the semipermeable membrane, and a first space located at one side of the semipermeable membrane and a second space located at the other side of the semipermeable membrane exist between the holding member and the semipermeable membrane, wherein the air guide cavity guides the airflow carrying the sample to flow into the first space, the sample carried by the airflow flowing into the first space enters the second space after being desorbed by the semipermeable membrane, and the second space is in fluid communication with the detection equipment.

3. The sample collecting and introducing device according to claim 2, wherein at least one of a concave part and a convex part is provided on a side surface of the holding member adjacent to the semipermeable membrane.

4. The sample collecting and introducing device according to claim 2, wherein the semipermeable membrane device further comprises an air pump, the air pump is in fluid communication with the first space to discharge the airflow that does not penetrates through the semipermeable membrane to the outside of the first space.

5. The sample collecting and introducing device according to claim 2, wherein the semipermeable membrane device further comprises a gas supply device, the gas supply device is in fluid communication with the second space to inject a carrier gas into the second space, and the carrier gas flows to the detection equipment after being mixed with the sample that is desorbed by the semipermeable membrane and enters the second space.

6. The sample collecting and introducing device according to claim 5, wherein the semipermeable membrane device further comprises a filtering device, the filtering device is arranged on a communication passage between the gas supply device and the second space to filter the carrier gas flowing from the gas supply device to the second space.

7. The sample collecting and introducing device according to claim 1, wherein the semipermeable membrane device further comprises a temperature control device, the temperature control device is configured to heat and cool the semipermeable membrane, so that the semipermeable membrane device enriches the sample at a relatively low temperature and desorbs the sample at a relatively high temperature.

8. The sample collecting and introducing device according to claim 1, further comprising a sample introducing tube, and the sample introducing tube is connected between the air guide cavity and the semipermeable membrane device.

9. The sample collecting and introducing device according to claim 1, wherein the semipermeable membrane device is arranged at the outside of the sampling device.

10. The sample collecting and introducing device according to claim 1, wherein the sampling device comprises an ejection part, the ejection part is configured to sweep the sample attached to the detected object through the airflow, and the swept sample flows to the air guide cavity under the drive of the airflow.

11. The sample collecting and introducing device according to claim 10, wherein the ejection part comprises an air pump, an air ejection cavity and an ejection hole, which are in fluid communication with each other successively, and the air pumped by the air pump is ejected toward the detected object through the air ejection cavity and the ejection hole.

12. The sample collecting and introducing device according to claim 10, wherein the sampling device further comprises a cyclone generation part, and the cyclone generation part is configured to generate cyclone and drive the sample swept by the ejection part to flow to the air guide cavity via the generated cyclone.

13. The sample collecting and introducing device according to claim 12, wherein the cyclone generation part comprises an air supplementing pump, an air supplementing cavity and a swirling hole, which are in fluid communication with each other successively, the air supplementing pump pumps airflow into the air supplementing cavity, and the swirling hole rotationally ejects the airflow entering the air supplementing cavity to form the cyclone.

14. The sample collecting and introducing device according to claim 13, wherein the swirling hole extends from the air supplementing cavity to the outer surface of the sampling device.

15. A detection system, comprising detection equipment and the sample collecting and introducing device according to claim 1, wherein the semipermeable membrane device of the sample collecting and introducing device is in fluid communication with the detection equipment.

* * * * *